US00PP08040P

United States Patent [19]

Jessel, Jr.

[11] Patent Number: Plant 8,040

[45] Date of Patent: Nov. 24, 1992

[54] CARNATION PLANT NAMED CFPC HI-LIGHT

[75] Inventor: Walter H. Jessel, Jr., Salinas, Calif.

[73] Assignee: California Florida Plant Co., L.P., Salinas, Calif.

[21] Appl. No.: 678,854

[22] Filed: Mar. 28, 1991

[51] Int. Cl.[5] ..... A01H 5/00

[52] U.S. Cl. ..... Plt./70.2

[58] Field of Search ..... Plt./70.1, 70.2, 70.5, Plt./70.6, 70.7, 71, 70

*Primary Examiner*—Howard J. Locker

*Attorney, Agent, or Firm*—Christie, Parker & Hale

[57] ABSTRACT

A new and unusual carnation producing flowers having cherry pink centers and white borders.

1 Drawing Sheet

SUMMARY OF THE INVENTION

The present invention relates to a new and distinct variety of carnation plant which was originated by me in a controlled breeding program by my crossing as seed parent, the variety known as 'French Can Can' and as pollen parent, the variety known as 'Claret Elegance'. The varietal denomination of this new carnation is 'CFPC Hi-Light'.

Among the novel characteristics possessed by the new variety which distinguishes it from its parents and all other varieties of which I am aware is its unusual flower coloration comprising cherry pink centers and white borders. Plants of the new variety have improved vigor and bud count as compared to its parent 'Claret Elegance'. CFPC Hi-Light has the disease resistance of its parent Claret Elegance but with more rapid flowering response, about 3½ to 4 months from planting to flowering.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety in different stages of development, depicted in color as nearly true as it is reasonably possible to make the same in a color illustration of this character.

DESCRIPTION OF THE NEW VARIETY

The new variety, CFPC Hi-Light, produces flowers which are resistant to soil-borne and air-borne diseases such as Alternaria sp. and the like. Flower color of the new variety is similar to Claret Elegance but flowers have more petals. CFPC Hi-Light produces large size spray-type flowers which open fully without bursting the calyx and causing splits which, together with the other characteristics heretofore and hereinafter described, make it especially suitable for commercial cut flower production as a spray.

The following is a detailed description of my new variety, with color terminology in accordance with the Royal Horticultural Society Colour Chart (RHSCC). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Hi-Light.

Classification:

*Botanical.*—*Dianthus caryophyllus.*

*Commercial.*—Carnation, suitable for greenhouse cut flower production as a spray.

Parentage:

*Female parent.*—'French Can Can'.

*Male parent.*—'Claret Elegance'.

PLANT

Height: About 33 inches.

Growing habit: Herbaceous, semi-upright.

Blooming habit: Terminal as a spray.

Blooming season: Year round.

Rooting time: 16 days.

Mutation prone: No.

Disease resistance: Resistant to Alternaria sp.

Temperature tolerance: Typical for carnation.

FOLIAGE

Color:

*Upper side.*—Near to 137A.

*Lower side.*—Near to 137A.

Size: About 5 inches long, about ½-inch wide at base of plant.

Quantity: Numerous.

Shape: Lanceolated, curled.

Texture: Smooth.

Ribs: Central, keeled.

Arrangement: Bi-lateral along stem.

Stem: Green.

BLOOM

Form: Circular, high.

Shape: Round, high crown.

Size:

*Diameter average.*—About 3¼ inches.

*Depth average.*—About 2⅛ inches.

Borne: Terminal as a spray.

Color:

*General tonality.*—Cherry pink with white border.

*Upper side.*—Near to from 57B to 57C.

*Lower side.*—Near to 57D.

*Center.*—Near to 57B.

*Outer petals.*—Near to 155D with subdued pinkish blush.

Keeping habit: Good.

Fragrance: Fragrant.

PETALS

Number: About 50.

Outer petals:

*Length.*—About 2¼ inches.

*Width.*—About 1½ inches.

Texture: Smooth.

Form: Fan shaped.

REPRODUCTIVE ORGANS

Filaments: About ¾-inch, white.

Anthers: Tan.

Pollen: Tanish yellow.

Styles: White.

Stigma: Light pink when mature.

Ovaries: Conical in shape, green changing to tan at tip.

I claim:

1. A new and distinct variety of carnation plant, substantially as shown and described, characterized particularly by flowers of attractive cherry pink and white coloration.

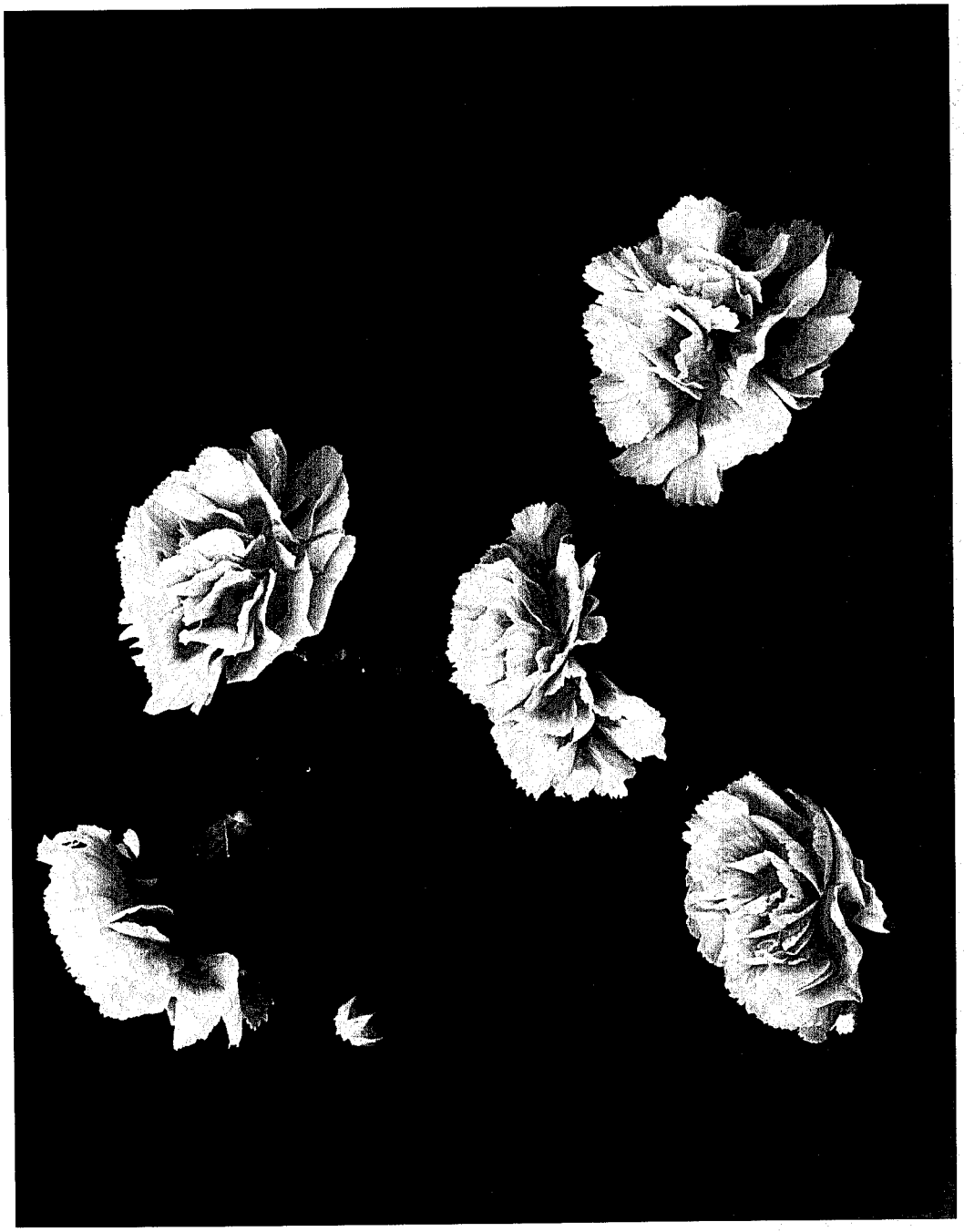

* * * * *